(12) United States Patent
Cho et al.

(10) Patent No.: US 8,252,507 B2
(45) Date of Patent: Aug. 28, 2012

(54) PHOTOACTIVE COMPOUND AND PHOTOSENSITIVE RESIN COMPOSITION COMPRISING THE SAME

(75) Inventors: Chang Ho Cho, Gyeonggi-do (KR); Sung Hyun Kim, Daejeon (KR); Raisa Kharbash, Daejeon (KR); Keon Woo Lee, Daejeon (KR); Sang Kyu Kwak, Daejeon (KR); Dong Kung Oh, Daejeon (KR); Chang Soon Lee, Daejeon (KR); Kyoung Hoon Min, Daejeon (KR)

(73) Assignee: LG Chem, Ltd., Seoul (KR)

( * ) Notice: Subject to any disclaimer, the term of this patent is extended or adjusted under 35 U.S.C. 154(b) by 298 days.

(21) Appl. No.: 12/743,373

(22) PCT Filed: Apr. 1, 2009

(86) PCT No.: PCT/KR2009/001660
§ 371 (c)(1),
(2), (4) Date: May 18, 2010

(87) PCT Pub. No.: WO2009/125940
PCT Pub. Date: Oct. 15, 2009

(65) Prior Publication Data
US 2010/0261815 A1    Oct. 14, 2010

(30) Foreign Application Priority Data

Apr. 10, 2008 (KR) .................. 10-2008-0033089
Apr. 10, 2008 (KR) .................. 10-2008-0033097

(51) Int. Cl.
*C07D 209/82* (2006.01)
*C08F 2/48* (2006.01)
*G03F 7/028* (2006.01)
*G03F 7/033* (2006.01)

(52) U.S. Cl. ............... 430/270.1; 430/919; 430/920; 522/63; 548/440

(58) Field of Classification Search .......... 430/270.1, 430/919, 920; 522/63; 548/440
See application file for complete search history.

(56) References Cited

U.S. PATENT DOCUMENTS
2006/0241259 A1 * 10/2006 Tanabe et al. .............. 526/217

FOREIGN PATENT DOCUMENTS
JP    2004359639 A  * 12/2004
JP    2007-286138 A    11/2007
JP    2007-286140 A    11/2007
JP    2007286138 A  * 11/2007
JP    2007286140 A  * 11/2007
WO    WO 2007/062963 A1    6/2007
WO    WO 2007062963 A1 *  6/2007

* cited by examiner

Primary Examiner — Satya Sastri
(74) Attorney, Agent, or Firm — McKenna Long & Aldridge LLP

(57) ABSTRACT

A novel photoactive compound is provided. The photoactive compound has a structure represented by Formula 1:

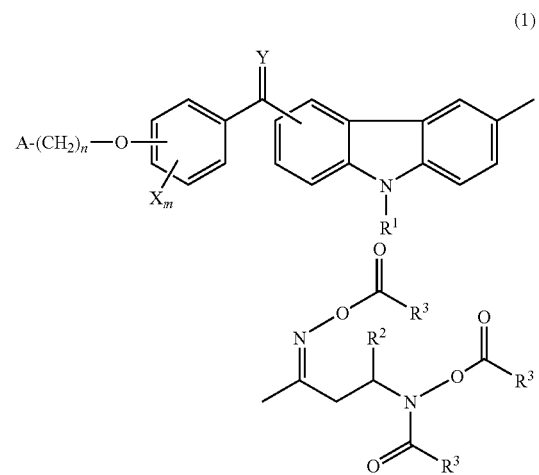

(1)

wherein $R^1$, $R^2$, $R^3$, A, X, Y, n and m are as defined in the specification.

The photoactive compound efficiently absorbs UV light. Accordingly, the photoactive compound has an improved ability to generate radicals and is efficiently photopolymerized with unsaturated bonds. Further provided is a photosensitive resin composition comprising the photoactive compound. The photosensitive resin composition has good sensitivity because it efficiently absorbs UV light. In addition, the photosensitive resin composition has excellent characteristics in terms of residual film ratio, mechanical strength and resistance to heat, chemicals and development. Therefore, the photosensitive resin composition is advantageously used in curing materials for column spacers, overcoats and passivation films of liquid crystal display devices. In addition, the photosensitive resin composition has excellent thermal processing characteristics.

16 Claims, No Drawings

PHOTOACTIVE COMPOUND AND PHOTOSENSITIVE RESIN COMPOSITION COMPRISING THE SAME

This application is a 35 U.S.C. §371 National Stage entry of International Application No. PCT/KR2009/001660, filed on Apr. 1, 2009, and claims priority to Korean Application Nos. 10-2008-0033089 and 10-2008-0033097, both filed on Apr. 10, 2008, which are all hereby incorporated by reference in their entireties.

BACKGROUND OF THE INVENTION

1. Field of the Invention

The present invention relates to a photoactive compound having a novel structure and a photosensitive resin composition comprising the same. More specifically, the present invention relates to a photoactive compound that has a high UV absorption rate, is excellent in sensitivity and thermal processing characteristics, and is highly compatible with other components in a photosensitive resin composition, and a photosensitive resin composition comprising the photoactive compound.

2. Description of the Related Art

Photoactive compounds refer to materials that are decomposed to generate chemically active atoms or molecules when they absorb light. Photoactive compounds are widely used in photosensitive resin compositions due to their ability to generate chemically active species. Examples of such chemically active species include acids, bases and radicals. Particularly, a photoactive compound capable of generating radicals is used together with a radically polymerizable acrylic group for the purpose of improving the strength of a coating film.

A typical photosensitive resin composition can be used for the formation of a pattern by the following procedure. First, the photosensitive resin composition is applied to a substrate to form a coating. A particular portion of the coating is exposed to light through a photomask. The coating is developed to remove the unexposed portion, leaving a pattern. Photosensitive resin compositions are currently used in the production of photocurable inks, photosensitive printing plates, a variety of photoresists, including color filter photoresists for LCDs, photoresists for resin black matrices and transparent photoresists, etc. because they can be polymerized and cured upon being irradiated with light.

Photosensitive resin compositions have been used in traditional applications, such as notebook computers and mobile devices. In recent years, an increasing demand for high quality LCDs in diverse applications has extended the applicability of photosensitive resin compositions to the fabrication of liquid crystal display devices for televisions and monitors. There also exists a strong need for photosensitive resin compositions that rapidly respond to light and have excellent mechanical properties to improve the productivity and durability of liquid crystal display devices.

High reactivity to light, i.e. photosensitivity, of a photosensitive resin composition is a very important factor in forming a pattern by photolithography or an insulating protective film by full exposure. Further, column spacers acting as supports or an overcoat and a passivation film acting as protective films should have excellent mechanical properties in order to exert their inherent performance characteristics without damage to a liquid crystal display device by an external impact.

Under such circumstances, there is a need for photopolymerization initiators with high photosensitivity. Even a small amount of a highly photosensitive photopolymerization initiator in a photosensitive resin composition can sufficiently increase the sensitivity of the photosensitive resin composition, which reduces the generation of sources contaminating liquid crystal, increases the residual film ratio of a pattern and broadens the choice of other raw materials for the preparation of the composition.

Acetophenone derivatives, benzophenone derivatives, biimidazole derivatives, acylphosphine oxide derivatives, triazine derivatives and oxime ester derivatives are known as photopolymerization initiators suitable for use in photosensitive resin compositions. Of these, oxime ester derivatives become colorless when they absorb UV light, have the ability to generate radicals, and are very stable in compositions.

Oxime ester structure-based photoinitiators have been developed, for example, α-oxooxime derivatives, combinations of thioxanthone and oxime ester compounds, oxime esters using p-dialkylaminobenzene as a synergist, photoinitiators using β-aminooxime, and oxime ether photoinitiators containing one or more ethylenically unsaturated groups in the molecular structure. These early oxime derivatives have the problem of low photoinitiation efficiency and are inefficient in UV absorption when they have good color characteristics.

Numerous efforts have been made to improve the photoinitiation efficiency of oxime derivatives. However, the oxime derivatives fail to sufficiently shorten the processing time to a satisfactory level. Particularly, the oxime derivatives do not sufficiently satisfy the degree of cure of films having a high pigment concentration or a coating having a thickness as large as 2.5 μm. Accordingly, there remains a difficulty in forming fine patterns using the oxime derivatives. Further, patterns formed using the oxime derivatives do not meet the critical dimension (CD) and mechanical strength required in final products.

Irgacure OXE 01 and Irgacure OXE 02, oxime ester-based photopolymerization initiators commercially available from Ciba Specialty Chemical, that are currently in use have markedly improved sensitivity. However, the Irgacure series are economically unfavorable because the sensitivity is not sufficient considering their high price. Another problem of Irgacure OXE 01 and Irgacure OXE 02 is poor storage stability.

Thus, there is a need to develop a photoactive compound as a photoinitiator that can efficiently absorb UV light even when used in a small amount and is excellent in sensitivity, thermal processing characteristics and solubility, and a photosensitive resin composition comprising such a photoactive compound.

SUMMARY OF THE INVENTION

The present inventors have earnestly conducted and intensively conducted research to solve the problems of conventional photoactive compounds as photopolymerization initiators and the problems associated with the use of the photoactive compounds in photosensitive resin compositions. As a result, the present inventors have found that a novel photoactive compound containing an oxime ester structure as a basic structure can efficiently absorb UV light of 365 nm (i-line) to effectively generate radicals, achieving desired sensitivity even when used in a small amount, and that a photosensitive resin composition using the photoactive compound as a photopolymerization initiator is excellent in sensitivity and thermal processing characteristics. The present invention has been achieved based on these findings.

It is an object of the present invention to provide a novel photoactive compound containing oxime ester moieties that can efficiently absorb UV light and is excellent in sensitivity and thermal processing characteristics.

It is another object of the present invention to provide a photosensitive resin composition comprising the photoactive compound as a photopolymerization initiator.

According to an aspect of the present invention, there is provided a photoactive compound represented by Formula 1:

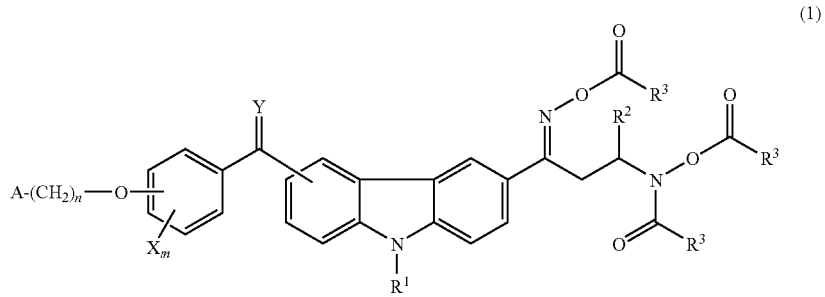

(1)

wherein $R^1$, $R^2$ and $R^3$ are each independently selected from the group consisting of a hydrogen atom, a halogen atom, OH, CN, R, OR, SR, COR, OCOR, NRR', CONRR' (in which R and R' are each independently $C_1$-$C_6$ alkyl; $C_1$-$C_6$ haloalkyl; $C_1$-$C_6$ alkyl group substituted with at least one group selected from the group consisting of $NL_2$, OL and SL (in which each L is hydrogen or $C_1$-$C_6$ alkyl)); a phenyl group unsubstituted or substituted with at least one group selected from the group consisting of $C_1$-$C_6$ alkyl, halogen atom, nitrile, OH and COOH; and a $C_2$-$C_5$ alkylcarboxylic acid group, X is selected from the group consisting of a hydrogen atom; a halogen atom; a $C_1$-$C_6$ alkyl group unsubstituted or substituted with at least one group selected from the group consisting of $NL_2$, OL and SL (in which each L is hydrogen or $C_1$-$C_6$ alkyl); a $C_1$-$C_6$ haloalkyl group; a phenyl group unsubstituted or substituted with at least one group selected from the group consisting of $C_1$-$C_6$ alkyl, halogen atom, nitrile, OH and COOH; and a $C_2$-$C_5$ alkylcarboxylic acid group, Y is an oxygen atom or N—O—CO—$R^3$, A is selected from the group consisting of a cycloalkyl group, an aryl group, and a heterocyclic ring unsubstituted or substituted with at least one halogen atom or alkyl group, n is from 0 to 6, and m is from 0 to 4.

According to another aspect of the present invention, there is provided a photosensitive resin composition comprising the photoactive compound of Formula 1, an alkali-soluble binder resin, a polymerizable compound having at least one ethylenically unsaturated bond, and a solvent.

DETAILED DESCRIPTION OF THE INVENTION

Exemplary embodiments of the present invention will now be described in more detail.

1. Photoactive Compound

The present invention provides a photoactive compound having a structure of Formula 1:

wherein $R^1$, $R^2$ and $R^3$ are each independently selected from the group consisting of a hydrogen atom, a halogen atom, OH, CN, R, OR, SR, COR, OCOR, NRR', CONRR' (in which R and R' are each independently $C_1$-$C_6$ alkyl; $C_1$-$C_6$ haloalkyl; $C_1$-$C_6$ alkyl group substituted with at least one group selected from the group consisting of $NL_2$, OL and SL (in which each L is hydrogen or $C_1$-$C_6$ alkyl)); a phenyl group unsubstituted or substituted with at least one group selected from the group consisting of $C_1$-$C_6$ alkyl, halogen atom, nitrile, OH and COOH; and a $C_2$-$C_5$ alkylcarboxylic acid group, X is selected from the group consisting of a hydrogen atom; a halogen atom; a $C_1$-$C_6$ alkyl group unsubstituted or substituted with at least one group selected from the group consisting of $NL_2$, OL and SL (in which each L is hydrogen or $C_1$-$C_6$ alkyl); a $C_1$-$C_6$ haloalkyl group; a phenyl group unsubstituted or substituted with at least one group selected from the group consisting of $C_1$-$C_6$ alkyl, halogen atom, nitrile, OH and COOH; and a $C_2$-$C_5$ alkylcarboxylic acid group, Y is an oxygen atom or N—O—CO—$R^3$, A is selected from the group consisting of a cycloalkyl group, an aryl group, and a heterocyclic ring unsubstituted or substituted with at least one halogen atom or alkyl group, n is from 0 to 6, and m is from 0 to 4.

In Formula 1, $R^1$ is preferably methyl or ethyl. The photoactive compound of Formula 1 wherein $R^1$ is methyl or ethyl is advantageous for its high solubility, ease of synthesis and low preparation cost.

In Formula 1, $R^2$ is preferably methyl or phenyl. The photoactive compound of Formula 1 wherein $R^2$ is methyl or phenyl can be synthesized using an easy-to-obtain starting material, such as crotonyl chloride and benzoyl chloride.

In Formula 1, $R^3$ is a group that is to be decomposed into radicals as active species when exposed to light. $R^3$ is especially preferably methyl or phenyl. Methyl or phenyl is struc-

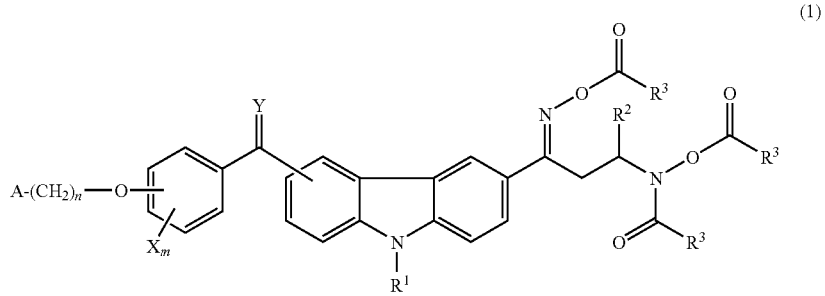

(1)

turally simple and highly mobile, thus improving the photo-initiation efficiency of the photoactive compound.

In Formula 1, X is preferably hydrogen or methyl, which helps to adjust the UV absorption wavelength to i-line.

In Formula 1, A is a group, that serves to increase the solubility of the photoactive compound and is preferably selected from the group consisting of cyclohexyl, 2,2-dimethyl-1,3-dioxolanyl and 2-tetrahydrofuryl groups. In the definition of A, the heterocyclic ring is selected from the group consisting of 1,3-dioxolanyl, 2-tetrahydrofuryl, 3-tetrahydrofuryl, 2-tetrahydrothienyl, 2-oxalyl, 2-furyl, 3-furyl, 2-thienyl, 2-pyridyl, 2-piranyl, 2-carbazolyl, and 2-pyrimidyl groups.

Since the photoactive compound of the present invention efficiently absorbs UV light of i-line (365 nm), the ability of the photoactive compound to generate radicals is improved. Accordingly, desired sensitivity can be obtained even when a small amount of the photoactive compound is used.

In addition, the photoactive compound of the present invention has excellent characteristics in terms of residual film ratio, mechanical strength and resistance to heat, chemicals and development due to its high photoinitiation efficiency. Therefore, a photosensitive resin composition comprising the photoactive compound is advantageously used in curing materials for column spacers, overcoats, passivation films, etc. of liquid crystal display devices. In addition, the photosensitive resin composition has excellent thermal processing characteristics.

The photoactive compound of the present invention is prepared by a method comprising the following steps.

(First Step)

An alkylcarbazole, a substituted benzoyl chloride, a substituted or unsubstituted crotonyl chloride are reacted in the presence of a Lewis acid in a solvent to prepare a first intermediate having a structure of Formula 2:

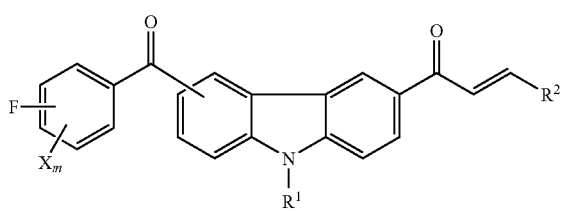

(2)

wherein $R^1$, $R^2$, X and m are as defined in Formula 1.

(Second Step)

An alkyl alcohol, tetrabutylammonium hydrogen sulfate, a solvent and a base are added to the first intermediate to prepare a second intermediate having a structure of Formula 3:

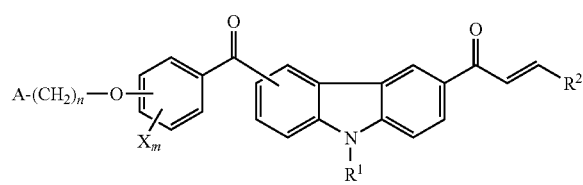

(3)

wherein $R^1$, $R^2$, X, A, n and m are as defined in Formula 1.

(Third Step)

$NH_2OH \cdot HCl$, a base and a solvent are added to the second intermediate to prepare a third intermediate having a structure of Formula 4:

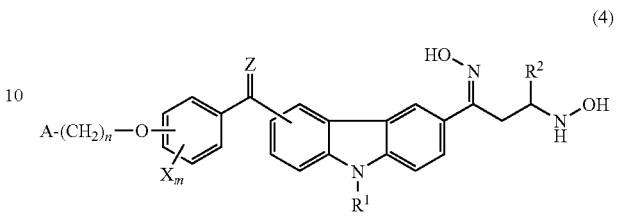

(4)

wherein $R^1$, $R^2$, X, A, n and m are as defined in Formula 1, and Z is an oxygen atom or N—OH.

(Fourth Step)

A compound containing $R^3$—C(O)—Cl or $R^3$—C(O)—O—C(O)—$R^3$ (in which $R^3$ is as defined in Formula 1), a solvent and a base are added to the third intermediate to prepare the photoactive compound of Formula 1. When Y is an oxygen atom (i.e. the photoactive compound of Formula 1 is a ketone), it may react with $NH_2OH \cdot HCl$ under particular conditions. As a result of the reaction, Y is converted to N—OH.

In the first step, the alkylcarbazole is preferably methylcarbazole or ethylcarbazole and the Lewis acid can be selected from aluminum chloride and zinc chloride.

There is no limitation on the kind of the solvent used in the first step. For example, the solvent may be dimethylformamide. The solvents used in the second and third steps can be selected from the group consisting of water and alcoholic solvents, such as methanol, ethanol and isopropanol. Among the alcoholic solvents, ethanol is most preferred taking into consideration the affinity for water, reaction exothermicity and toxicity, solubility, etc. The solvent used in the fourth step is not particularly limited. For example, preferred is a solvent that readily dissolves the reactants and the product and is easily removable under vacuum. Examples of such solvents include dichloromethane, chloroform, tetrahydrofuran, diethyl ether and ethyl acetate.

The bases used in the second and third steps can be selected from sodium hydroxide and sodium acetate. In each of the second and third steps, the base may be diluted with an appropriate amount of water. The base used in the fourth step is preferably an amine that can neutralize toxic HCl during the reaction to form a salt, but it is not limited thereto.

2. Photosensitive Resin Composition

The present invention also provides a photosensitive resin composition comprising the photoactive compound of Formula 1 as a photopolymerization initiator, an alkali-soluble binder resin, a polymerizable compound having at least one ethylenically unsaturated bond, and a solvent.

The photoactive compound of Formula 1 is preferably present in an amount of 0.1 to 5% by weight, based on the total weight of the photosensitive resin composition. If the amount of the photoactive compound is less than 0.1% by weight, sufficient sensitivity cannot be expected. Meanwhile, if the amount of the photoactive compound exceeds 5% by weight, UV light cannot reach the bottom of the photosensitive resin composition owing to the high UV absorption of the photoactive compound.

The alkali-soluble binder resin may be a copolymer of a monomer having at least one acid functional group and a monomer copolymerizable therewith, or a compound prepared by polymerizing the copolymer with an ethylenically unsaturated compound containing at least one epoxy group.

The monomer having at least one acid functional group is preferably selected from the group consisting of, but not limited to, (meth)acrylic acid, crotonic acid, itaconic acid, maleic acid, fumaric acid, monomethyl maleic acid, isoprene sulfonic acid, styrene sulfonic acid, 5-norbornene-2-carboxylic acid, mono-2-((meth)acryloyloxy)ethyl phthalate, mono-2-((meth)acryloyloxy)ethyl succinate, ω-carboxy-polycaprolactone mono(meth)acrylate, and mixture thereof.

The monomer copolymerizable with the monomer having at least one acid functional group is selected from the group consisting of, but not limited to: unsaturated carboxylic acid esters, such as benzyl(meth)acrylate, methyl(meth)acrylate, ethyl(meth)acrylate, butyl(meth)acrylate, dimethylaminoethyl(meth)acrylate, isobutyl(meth)acrylate, t-butyl(meth)acrylate, cyclohexyl(meth)acrylate, isobornyl(meth)acrylate, ethylhexyl acrylate, 2-phenoxyethyl(meth)acrylate, tetrahydrofurfuryl(meth)acrylate, hydroxyethyl(meth)acrylate, 2-hydroxypropyl(meth)acrylate, 2-hydroxy-3-chloropropyl (meth)acrylate, 4-hydroxybutyl(meth)acrylate, acyloctyloxy-2-hydroxypropyl(meth)acrylate, glycerol(meth)acrylate, 2-methoxyethyl(meth)acrylate, 3-methoxybutyl(meth)acrylate, ethoxydiethylene glycol(meth)acrylate, methoxytriethylene glycol(meth)acrylate, methoxytripropylene glycol(meth)acrylate, poly(ethylene glycol)methyl ether (meth)acrylate, phenoxydiethylene glycol(meth)acrylate, p-nonylphenoxypolyethylene glycol (meth)acrylate, p-nonylphenoxypolypropylene glycol(meth)acrylate, tetrafluoropropyl(meth)acrylate, 1,1,1,3,3,3-hexafluoroisopropyl (meth)acrylate, octafluoropentyl(meth)acrylate, heptadecafluorodecyl(meth)acrylate, tribromophenyl(meth)acrylate, methyl α-hydroxymethyl acrylate, ethyl α-hydroxymethyl acrylate, propyl α-hydroxymethyl acrylate, butyl α-hydroxymethyl acrylate, dicyclopentanyl(meth) acrylate, dicyclopentenyl(meth)acrylate, dicyclopentanyl oxyethyl(meth)acrylate, and dicyclopentenyl oxyethyl(meth) acrylate; vinyl aromatic monomers, such as styrene, α-methylstyrene, o-vinyltoluene, m-vinyltoluene, p-vinyltoluene, o-methoxystyrene, m-methoxystyrene, p-methoxystyrene, o-chlorostyrene, m-chlorostyrene, and p-chlorostyrene; unsaturated ethers, such as vinyl methyl ether, vinyl ethyl ether, and allyl glycidyl ether; N-vinyl tertiary amines, such as N-vinyl pyrrolidone, N-vinyl carbazole, and N-vinyl morpholine; unsaturated imides, such as N-phenylmaleimide, N-(4-chlorophenyl)maleimide, N-(4-hydroxyphenyl)maleimide, and N-cyclohexylmaleimide; maleic anhydrides, such as maleic anhydride and methyl maleic anhydride; unsaturated glycidyl compounds, such as allyl glycidyl ether, glycidyl (meth)acrylate, and 3,4-epoxycyclohexylmethyl(meth) acrylate; and mixtures thereof.

The alkali-soluble binder resin has an acid value of about 30 to about 300 KOH mg/g. The alkali-soluble binder resin preferably has a weight average molecular weight of 1,000 to 200,000 and more preferably 5,000 to 100,000.

The polymerizable compound having at least one ethylenically unsaturated bond may be any of those known in the art. For example, the polymerizable compound is selected from the group consisting of, but not limited to: compounds obtained by esterifying an α,β-unsaturated carboxylic acid with a polyhydric alcohol, such as ethylene glycol di(meth) acrylate, polyethylene glycol di(meth)acrylate having 2 to 14 ethylene groups, trimethylolpropane di(meth)acrylate, trimethylolpropane tri(meth)acrylate, pentaerythritol tri(meth) acrylate, pentaerythritol tetra(meth)acrylate, 2-trisacryloyloxymethylethylphthalic acid, propylene glycol di(meth) acrylate having 2 to 14 propylene groups, dipentaerythritol penta(meth)acrylate, dipentaerythritol hexa(meth)acrylate, and a mixture of an acid modified product of dipentaerythritol penta(meth)acrylate and an acid modified product of dipentaerythritol hexa(meth)acrylate; compounds obtained by adding (meth)acrylic acid to a glycidyl group-containing compound, such as a trimethylolpropane triglycidyl ether acrylic acid adduct and a bisphenol A diglycidyl ether acrylic acid adduct; esterified products of a compound having at least one hydroxyl group or ethylenically unsaturated bond, such as phthalic acid diester of β-hydroxyethyl(meth)acrylate or a toluene diisocyanate adduct of β-hydroxyethyl(meth)acrylate, with a polyvalent carboxylic acid, and adducts thereof with polyisocyanate, the compound having at least one ethylenically unsaturated bond being selected from the group consisting of allyl glycidyl ether, glycidyl(meth)acrylate, 3,4-epoxycyclohexylmethyl(meth)acrylate, glycidyl 5-norbornene-2-methyl-2-carboxylate (mixture of endo- and exo-isomers), 1,2-epoxy-5-hexene, 1,2-epoxy-9-decene and mixtures thereof; alkyl esters of (meth)acrylic acid, such as methyl(meth)acrylate, ethyl(meth)acrylate, butyl(meth)acrylate and 2-ethylhexyl(meth)acrylate; 9,9'-bis[4-(2-acryloyloxyethoxy)phenyl]fluorene; and mixtures thereof.

If needed, these polymerizable compounds may contain a silica dispersion. Commercially available silica dispersions are Nanocryl XP series 0596, 1045 and 21/1364 and Nanopox XP series 0516 and 0525, all of which are sold by Hanse Chemie GmbH.

The solvent is selected from the group consisting of, but not limited to, methyl ethyl ketone, methyl cellosolve, ethyl cellosolve, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, 2-ethoxypropanol, 2-methoxypropanol, 3-methoxybutanol, cyclopentanone, cyclohexanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, dipropylene glycol monomethyl ether, and mixtures thereof.

The photosensitive resin composition of the present invention preferably comprises 0.1 to 5% by weight of the photoactive compound of Formula 1, 1 to 20% by weight of the alkali-soluble binder resin, 0.5 to 20% by weight of the polymerizable compound having at least one ethylenically unsaturated bond, and 10 to 95% by weight of the solvent.

Optionally, the photosensitive resin composition of the present invention may further comprise one or more additives selected from another photoactive compound, a curing accelerator, a thermal polymerization inhibitor, a plasticizer, an adhesion promoter, a filler, and a surfactant.

The additional photoactive compound is selected from the group consisting of, but not limited to: triazine compounds, such as 2,4-trichloromethyl-(4'-methoxyphenyl)-6-triazine, 2,4-trichloromethyl-(4'-methoxystyryl)-6-triazine, 2,4-trichloromethyl-(piperonyl)-6-triazine, 2,4-trichloromethyl-(3',4'-dimethoxyphenyl)-6-triazine, 3-{-4-[2,4-bis(trichloromethyl)-s-triazin-6-yl]phenylthio}propanoic acid, 2,4-trichloromethyl-(4'-ethylbiphenyl)-6-triazine, and 2,4-trichloromethyl-(4'-methylbiphenyl)-6-triazine; biimidazole compounds, such as 2,2'-bis(2-chlorophenyl)-4,4',5,5'-tetraphenylbiimidazole, and 2,2'-bis(2,3-dichlorophenyl)-4,4',5,5'-tetraphenylbiimidazole; acetophenone compounds, such as 2-hydroxy-2-methyl-1-phenylpropan-1-one, 1-(4-isopropylphenyl)-2-hydroxy-2-methylpropan-1-one, 4-(2-hydroxyethoxy)-phenyl (2-hydroxy)propyl ketone, 1-hydroxycyclohexyl phenyl ketone, 2,2-dimethoxy-2-phenyl acetophenone, 2-methyl-(4-methylthiophenyl)-2-morpholino-1-propan-1-one (Irgacure-907), and 2-benzyl-2-dimethylamino-1-(4-morpholinophenyl)-butan-1-one (Irgacure-369); O-acyloxime compounds, such as Irgacure OXE 01 and Irgacure OXE 02, both of which are commercially available from Ciba Geigy; benzophenone compounds, such as 4,4'-bis(dimethylamino)benzophenone and 4,4'-bis(diethylamino)benzophenone; thioxanthone compounds, such as 2,4-diethyl thioxanthone, 2-chlorothioxanthone, isopropylthioxanthone and diisopropylthioxanthone; phosphine oxide compounds, such as 2,4,6-trimethylbenzoyldiphenylphosphine oxide, bis(2,6-dimethoxybenzoyl)-2,4,4-trimethylpentylphosphine oxide, and bis(2,6-dichlorobenzoyl)propylphosphine oxide; coumarin compounds, such as 3,3'-carbonylvinyl-7-(diethylamino)coumarin, 3-(2-benzothiazolyl)-7-(diethylamino)coumarin, 3-benzoyl-7-(diethylamino)coumarin, 3-benzoyl-7-methoxy-coumarin, and 10,10'-carbonylbis[1,1,7,7-tetramethyl-2,3,6,7-tetrahydro-1H,5H,11H—Cl]-benzopyrano[6,7,8-ij]-quinolizin-11-one; and mixtures thereof.

The curing accelerator may be any of those known in the art. For example, the curing accelerator is selected from the group consisting of, but not limited to, 2-mercaptobenzoimidazole, 2-mercaptobenzothiazole, 2-mercaptobenzooxazole, 2,5-dimercapto-1,3,4-thiadiazole, 2-mercapto-4,6-dimethylaminopyridine, pentaerythritol tetrakis(3-mercaptopropionate), pentaerythritol tris(3-mercaptopropionate), pentaerythritol tetrakis(2-mercaptoacetate), pentaerythritol tris(2-mercaptoacetate), trimethylolpropane tris(2-mercaptoacetate), trimethylolpropane tris(3-mercaptopropionate), trimethylolethane tris(2-mercaptoacetate), trimethylolethane tris(3-mercaptopropionate), and mixtures thereof.

The thermal polymerization inhibitor may be any of those known in the art. For example, the thermal polymerization inhibitor is selected from the group consisting of, but not limited to: p-anisole, hydroquinone, pyrocatechol, t-butylcatechol, N-nitrosophenylhydroxylamine ammonium salt, N-nitrosophenylhydroxylamine aluminum salt, phenothiazine, and mixtures thereof.

The plasticizer, the adhesion promoter, the filler and the surfactant may be any of those used in conventional photosensitive resin compositions.

In this case, the photosensitive resin composition preferably comprises 0.1 to 5% by weight of the additional photoactive compound and 0.01 to 5% by weight of the other additive(s).

The photosensitive resin composition of the present invention can be applied to a suitable support by any suitable process, such as roll coating, curtain coating, spin coating, slot die coating, printing or dipping. The support may be a metal, paper, glass or plastic substrate.

The coating formed on the support may be directly transferred to another support. Alternatively, the coating formed on the support may be indirectly transferred to another support via a blanket. There is no particular limitation on the application method of the photosensitive resin composition.

The photosensitive resin composition of the present invention can be cured under a suitable light source, such as a mercury vapor, carbon or xenon (Xe) arc that emits light having a wavelength of 250 to 450 nm.

The photosensitive resin composition of the present invention can be used in photocurable paints, photocurable inks, pigment dispersion type photoresists for the production of thin film transistor-liquid crystal display (TFT-LCD) color filters, photoresists for the formation of black matrices of TFT-LCDs, and photoresists for the formation of black matrices of organic light emitting diodes. No limitation is imposed on the application of the photosensitive resin composition according to the present invention.

Hereinafter, the following examples are provided to assist in a further understanding of the invention and are not intended to limit the scope of the invention.

EXAMPLES

Example 1

Preparation of Photoactive Compound 1

(1) Preparation of 4-fluorobenzoyl Chloride 1b

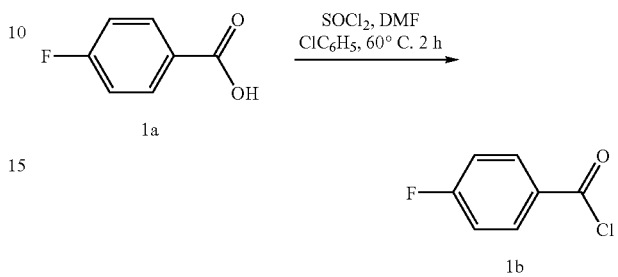

Thionyl chloride (3.8 g, 32.1 mmol) was slowly added to a solution of 4-fluorobenzoic acid 1a (3.0 g, 21.4 mmol) and N,N-dimethylformamide (5 drops) in 15 mL of chlorobenzene under a stream of nitrogen gas. The mixture was stirred at 60° C. for 2 hr. The solvent was removed under reduced pressure to afford 4-fluorobenzoyl chloride 1b. Yield: 3.0 g (88%).

$^1$H NMR (500 MHz, CDCl$_3$, ppm) 8.16-8.13 (2H, m, ArH), 7.20-7.16 (2H, m, ArH)

(2) Preparation of 1d

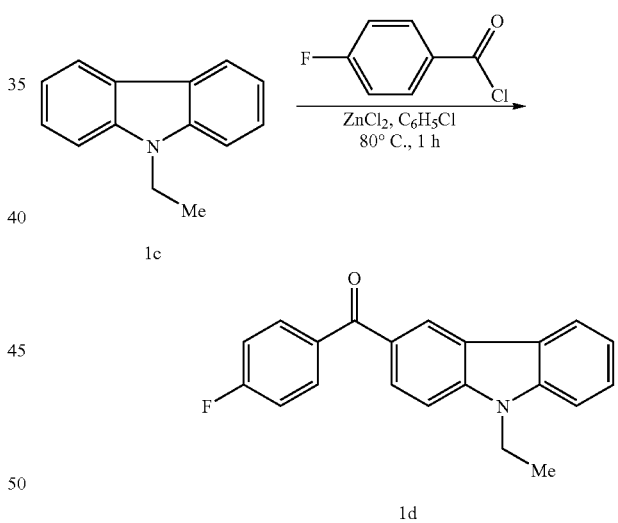

A mixture of N-ethylcarbazole (2.7 g, 13.8 mmol), zinc chloride (0.17 g, 1.2 mmol) and chlorobenzene (10 mL) was heated to 80° C., and then the compound 1b (2.0 g, 12.6 mol) was slowly added dropwise thereto. The resulting mixture was stirred at 80° C. for 1 hr. The reaction mixture was allowed to cool to room temperature. N-hexane (20 g) and water (30 g) were added to the reaction mixture. The organic layer was separated and dried over anhydrous sodium sulfate. After the solvent was removed under vacuum, the residue was purified by column chromatography (hexane/ethyl acetate=9/1), affording the acylated product 1d. Yield: 1.6 g (41%).

$^1$H NMR (500 MHz, CDCl$_3$, ppm) 8.57 (1H, s, ArH), 8.12-8.10 (1H, d, ArH), 8.00-7.98 (1H, d, ArH), 7.89-7.86 (2H, dd, ArH), 7.54-7.51 (1H, t, ArH), 7.47-7.44 (2H, dd, ArH), 7.30-7.27 (1H, t, ArH), 7.21-7.17 (2H, t, ArH), 4.44-4.39 (2H, q, CH$_2$CH$_3$), 1.49-1.46 (3H, t, CH$_2$CH$_3$)

(3) Preparation of 1e

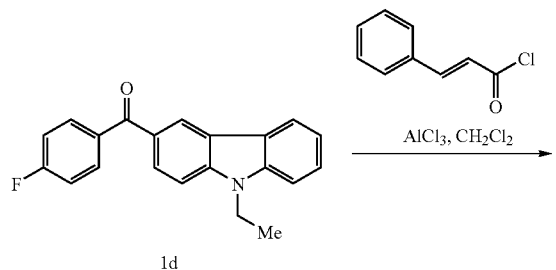

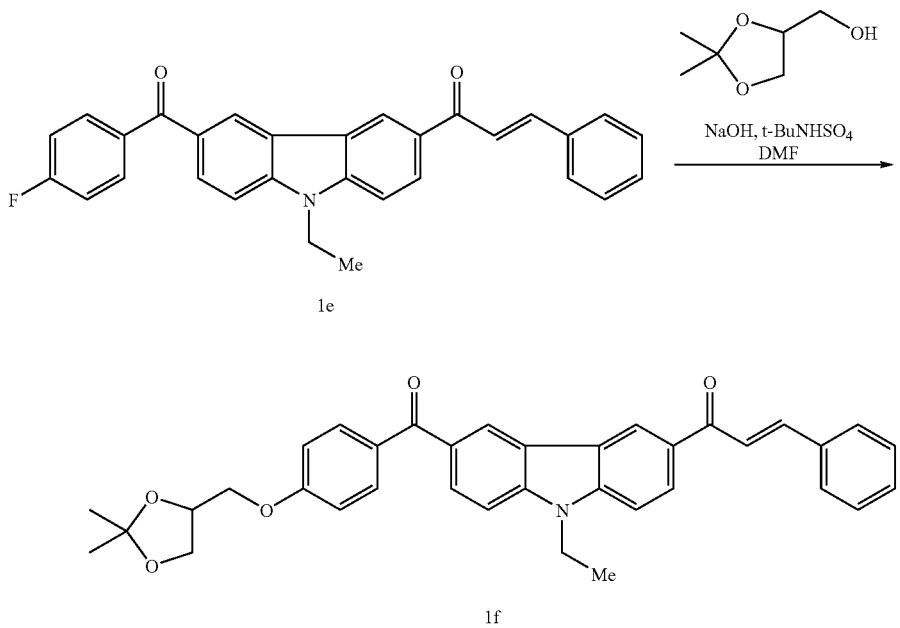

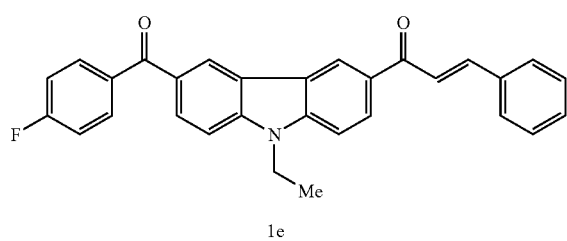

The compound 1d (2.1 g, 6.6 mol) and cinnamoyl chloride (1.2 g, 7.2 mmol) were dissolved in dichloromethane (30 mL), and then aluminum chloride (1.9 g, 14.2 mmol) was slowly added portionwise thereto at 0~10° C. The mixture was stirred at the same temperature for 2 hr. The mixture was allowed to warm to room temperature. After the mixture was further stirred for 12 hr at room temperature, the reaction mixture was poured into ice-water in a beaker. The organic layer was extracted, washed with saturated aqueous NaHCO$_3$, and dried over anhydrous sodium sulfate. After the solvent was removed under vacuum, the residue was purified by column chromatography (hexane/ethyl acetate=9/1), affording the acylated product 1e. Yield: 2.0 g (68%).

$^1$H NMR (500 MHz, CDCl$_3$, ppm) 8.83 (1H, s, ArH), 8.64 (1H, s, ArH), 8.29-8.27 (1H, d, ArH), 8.06-8.04 (1H, d, ArH), 7.91-7.88 (2H, m, ArH), 7.90-7.87 (1H, d, —CH═CH—), 7.76-7.73 (1H, d, —CH═CH—), 7.72-7.70 (2H, d, ArH), 7.53-7.50 (2H, m, ArH), 7.46-7.42 (3H, m, ArH), 7.23-7.20 (2H, t, ArH), 4.48-4.43 (2H, q, CH$_2$CH$_3$), 1.53-1.50 (3H, t, CH$_2$CH$_3$)

(4) Preparation of 1f

The compound 1e (2.0 g, 4.2 mmol), 2,2-dimethyl-1,3-dioxolane-4-methanol (1.2 g, 8.8 mmol) and tetrabutylammonium hydrogen sulfate (0.3 g, 0.8 mmol) were dissolved in 15 mL of N,N-dimethylformamide, and then sodium hydroxide (0.4 g, 11 mmol) was added thereto at room temperature under a stream of nitrogen gas. The mixture was stirred at 60° C. for 3 hr. The reaction mixture was allowed to cool to room temperature. Water (100 mL) was added to the reaction mixture to obtain a precipitate. The precipitate was collected, filtered, washed with water, and recrystallized from ethanol, affording the compound 1f. Yield: 1.8 g (78%).

$^1$H NMR (500 MHz, CDCl$_3$, ppm) 8.84 (1H, s, ArH), 8.64 (1H, s, ArH), 8.30-8.28 (1H, d, ArH), 7.91-7.88 (1H, d, —CH═CH—), 7.89-7.88 (2H, d, ArH), 7.78-7.74 (1H, d, —CH═CH—), 7.73-7.71 (2H, d, ArH), 7.54-7.51 (2H, m, ArH), 7.46-7.42 (3H, m, ArH), 7.05-7.04 (2H, d, ArH), 4.57-4.52 (1H, m, —CH—), 4.49-4.45 (2H, q, CH$_2$CH$_3$), 4.23-4.16 (2H, m, —HCH—), 4.09-4.05 (1H, dd, —CH—), 3.97-3.94 (1H, dd, —CH—), 1.54-1.51 (3H, t, CH$_2$CH$_3$), 1.49 (3H, s, CH$_3$CCH$_3$), 1.43 (3H, s, CH$_3$CCH$_3$)

(5) Preparation of Photoactive Compound 1

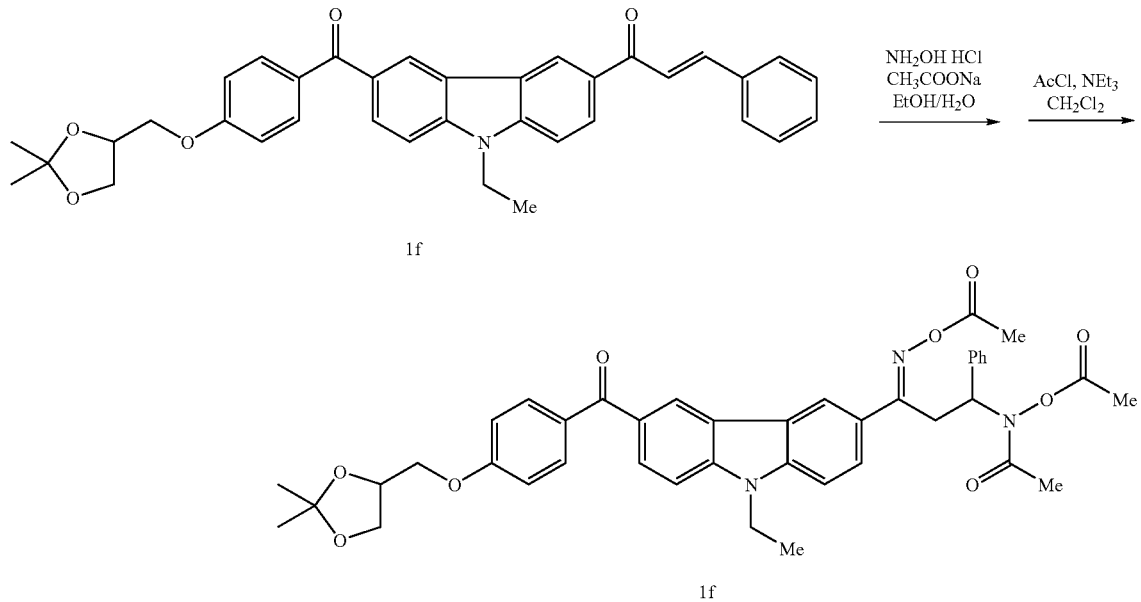

A solution of the compound 1f (0.6 g, 1 mmol) in 40 mL of ethanol was added to a solution of hydroxylamine hydrochloride (0.3 g, 4.3 mmol) and sodium acetate (0.35 g, 4.3 mmol) in 5 mL of water. The mixture was stirred under reflux for 3 hr. The progress of the reaction was confirmed by TLC (hexane/ethyl acetate=3/1). After completion of the reaction, 40 mL of water was added to the reaction mixture to give a white solid. The solid was filtered, washed with water, and dried. The product and triethylamine (0.32 g, 3.3 mmol) were dissolved in 10 mL of dichloromethane. Acetyl chloride (0.24 g, 3.3 mmol) was added to the dichloromethane solution. The resulting mixture was stirred at room temperature for 3 hr. The reaction mixture was extracted with dichloromethane. The organic layer was dried over anhydrous sodium sulfate and the solvent was removed under reduced pressure. The residue was purified by column chromatography (dichloromethane/methanol=9.5/0.5), affording the target compound 1. Yield: 0.5 g (61%).

$^1$H NMR (500 MHz, CDCl$_3$, ppm) 8.53 (1H, s, ArH), 8.34 (1H, s, ArH), 8.04-8.02 (1H, d, ArH), 7.88-7.86 (1H, d, ArH), 7.87-7.85 (2H, d, ArH), 7.49-7.44 (2H, d, ArH), 7.32-7.26 (5H, m, ArH), 7.04-7.02 (2H, d, ArH), 5.89 (1H, s, —NCH—), 4.56-4.51 (1H, m, —CH—), 4.46-4.42 (2H, q, —CH$_2$CH$_3$), 4.22-4.19 (1H, m, —CH—), 4.17-4.14 (1H, m, —CH—), 4.07-4.04 (1H, m, —CH—), 3.96-3.93 (1H, m, —CH—), 3.81-3.77 (1H, m, —NCH—HCH—), 3.71-3.67 (1H, m, —NCH—HCH—), 2.27 (3H, s, —COCH$_3$), 2.02 (3H, s, —COCH$_3$), 1.82 (3H, s, —COCH$_3$) 1.50-1.47 (3H, t, —CH$_2$CH$_3$), 1.49 (3H, s, CH$_3$CCH$_3$), 1.42 (3H, s, CH$_3$CCH$_3$)

Comparative Example 1

Irgacure OXE-02 (Ciba Specialty Chemical) was used.

Comparative Example 2

(1) Aluminum bromide (0.9 g, 0.0034 mol) was added to a solution of 4-cyanobenzaldehyde (5 g, 0.034 mol) in trichloroacetonitrile (100 g, 0.688 mol). Dry hydrochloric acid gas was passed through the mixture at −10° C. for 2 hr. Then, the resulting mixture was stirred at room temperature for 1 day. The trichloroacetonitrile was removed under reduced pressure, giving a mixture of 2,4-trichloromethyl-(4'-acetylphenyl)-6-triazine 2a and 2,4,6-tris(trichloromethyl)-1,3,5-triazine as a by-product. The two products were used for the next step without isolation because they have almost the same solubility in any solvent.

(2) A solution of the compound 2a and the 2,4,6-tris(trichloromethyl)-1,3,5-triazine (7.6 g) in 90 ml of ethanol was added to a solution of hydroxylamine hydrochloride (1.3 g, 19.2 mmol) and sodium acetate (1.8 g, 22.7 mmol) in 30 mL of water. The mixture was stirred under reflux for 1 hr. The progress of the reaction was confirmed by TLC (hexane/ethyl acetate=3/1). After completion of the reaction, the 2,4,6-tris(trichloromethyl)-1,3,5-triazine was filtered off and 500 mL of water was added to the filtrate to precipitate 2,4-trichloromethyl-(4'-acetylphenyloxime)-6-triazine 2b. The precipitate was filtered, washed with water, and dried.

(3) Preparation of 2,4-trichloromethyl-(4'-acetylphenylacetoxime)-6-triazine

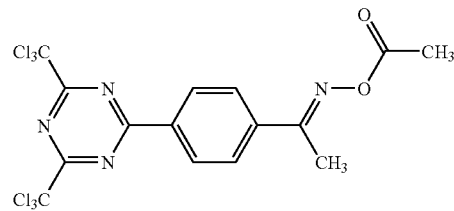

Acetic anhydride (1.1 g, 11.5 mmol) was added to a solution of the compound 2b (4.7 g, 10.4 mmol) and triethylamine (1.1 g, 11.5 mmol) in 60 ml of dichloromethane. The mixture was stirred at room temperature for 1 day. The solvent was removed under reduced pressure. Ethanol treatment of the residue afforded the target compound.

Comparative Example 3

(1) Preparation of 2,4-trichloromethyl-(4'-dibromomethylbiphenyl)-6-triazine 4a

N-Bromosuccinimide (1.5 g, 8.2 mmol) and 2,2'-azobisbutyronitrile (0.1 g) were added to a solution of 2,4-trichloromethyl-(4'-methylbiphenyl)-6-triazine (TAZ-204, Midori Kagaku Co. Ltd.) (2 g, 4.1 mmol) in a 20 mL of carbon tetrachloride. The mixture was allowed to react under reflux for 2 hr. The progress of the reaction was confirmed by TLC (hexane/ethyl acetate=3/1). After completion of the reaction, the precipitate was filtered off and the filtrate was concentrated under reduced pressure. Thereafter, the concentrate was treated with ethanol, affording 2,4-trichloromethyl-(4'-dibromomethylbiphenyl)-6-triazine 4a as a crystal. Yield: 2.2 g (84%).

$^1$H NMR (500 MHz, CDCl3, ppm) 8.78-8.76 (2H, d, ArH), 7.81-7.79 (2H, d, ArH), 7.72-7.68 (4H, dd, ArH), 6.72 (1H, s, CHBr$_2$)

(2) Preparation of 2,4-trichloromethyl-(4'-formylbiphenyl)-6-triazine 4b

A solution of silver nitrate (0.53 g, 3.1 mmol) in 5 mL of water was added to a solution of the compound 4a (1 g, 1.5 mmol) in 20 ml of ethanol. The mixture was stirred under reflux for 1.5 hr. The hot reaction solution was filtered to remove the precipitate and the filtrate was cooled. The cooled filtrate was filtered, affording 2,4-trichloromethyl-(4'-formylbiphenyl)-6-triazine 4b as a white crystal. Yield: 0.6 g (81%).

$^1$H NMR (500 MHz, CDCl3, ppm) 10.10 (1H, s, CHO), 8.81-8.79 (2H, d, ArH), 8.03-8.01 (2H, d, ArH), 7.86 7.84 (4H, d, ArH)

(3) Preparation of 2,4-trichloromethyl-(4'-formyloximebiphenyl)-6-triazine 4c

A solution of the compound 4b (1.3 g, 2.6 mmol) in 30 mL of ethanol was added to a solution of hydroxylamine hydrochloride (0.2 g, 2.8 mmol) and sodium acetate (0.27 g, 3.3 mmol) in 10 mL of water. The mixture was stirred at reflux for 1 hr. The progress of the reaction was confirmed by TLC (hexane/ethyl acetate=3/1). Water (100 ml) was added to the reaction mixture to obtain a precipitate. The precipitate was filtered, washed with water and dried, affording 2,4-trichloromethyl-(4'-formyloximebiphenyl)-6-triazine 4c as a white solid. Yield: 1.1 g (84%).

$^1$H NMR (500 MHz, DMSO, ppm) 11.38 (1H, s, NOH), 8.64-8.62 (2H, d, ArH), 8.22 (1H, s, H—C=N), 8.06-8.04 (2H, d, ArH), 7.88-7.86 (2H, d, ArH), 7.76-7.74 (2H, d, ArH)

(4) Preparation of 2,4-trichloromethyl-(4'-formylbiphenylacetoxime)-6-triazine 4

Acetic anhydride (0.24 g, 2.3 mmol) was added to a solution of the compound 4c (1.1 g, 2.1 mmol) and triethylamine (0.23 g, 2.3 mmol) in 20 mL of dichloromethane. The mixture was stirred at room temperature for one day. The solvent was removed under reduced pressure. The residue was treated with ethanol, affording the target compound 4. Yield: 0.8 g (68%).

$^1$H NMR (500 MHz, CDCl13, ppm) 8.78-8.77 (2H, d, ArH), 8.42 (1H, s, H—C=N), 7.88-7.87 ((2H, d, ArH), 7.84-7.82 (2H, d, ArH), 7.76-7.74 (2H, d, ArH), 2.26 (3H, s, O=CCH$_3$)

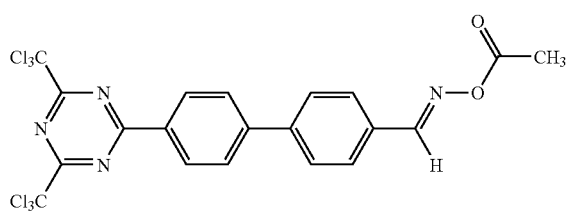

Experimental Example 1

Solubility Measurement

The solubilities of Irgacure OXE-02 (Ciba Specialty Chemical) of Comparative Example 1, the compounds of Comparative Examples 2-3, and the compound of Example 1, which contains oxime ester moieties, were measured in various solvents, including propylene glycol methyl ether acetate (PGMEA), dipropylene glycol methyl ether (DPM), 3-methoxybutyl acetate (MBA), ethyl-3-ethoxy propionate (EEP) and cyclohexanone (CH). The solubility of each of the compounds was determined by measuring the amount (g) of the compound completely dissolved in the corresponding solvent. The measurement results are shown in Table 1.

TABLE 1

| Photoinitiator | PGMEA | DPM | 3-MBA | EEP | CH |
| --- | --- | --- | --- | --- | --- |
| Example 1 | 20 | 7 | 13 | 15 | 60 |
| Comparative Example 1 | 12 | 5 | 10 | 10 | 40 |
| Comparative Example 2 | 7 | 3 | 5 | 6 | 25 |
| Comparative Example 3 | 7 | 2 | 5 | 5 | 20 |

Experimental Example 2

Sensitivity Measurement 12 g of benzyl methacylate/methacrylic acid (BzMA/MAA) (molar ratio=70/30, Mw: 20,000) as an alkali-soluble resin binder, 12 g of dipentaerythritol hexaacrylate as a polymerizable compound, 1 g of each of the compounds of Example 1 and Comparative Examples 1-3 as a photopolymerization initiator, and 75 g of PGMEA as an organic solvent were mixed together using a shaker for 3 hr. The mixture was filtered through a filter (size=5 microns) to prepare a photosensitive composition in the form of a solution. The photosensitive composition was applied to glass by spin coating to form a 2.5 µm thick thin film. The thin film was heated on a hot plate at 100° C. for 2 min to remove the solvent. The thin film was exposed under a high-pressure mercury lamp at an exposure dose of 20 mW/cm$^2$ for 5 sec. FT-IR analysis of the thin film was conducted before and after the exposure to determine the acrylate conversion. The experimental results are shown in Table 2.

TABLE 2

| Photoinitiator | Acrylate conversion (%) |
| --- | --- |
| Example 1 | 40 |
| Comparative Example 1 | 38 |
| Comparative Example 2 | 36 |
| Comparative Example 3 | 39 |

The experimental results show that the sensitivity and solubility of the photoinitiator of Example 1 were better than those of the photoinitiators of Comparative Examples 1-3.

Example 2

Preparation of Transparent Photosensitive Resin Composition 12 g of a copolymer of benzyl methacylate/methacrylic acid (BzMA/MAA) (molar ratio=70/30, Mw: 24,000) as an alkali-soluble binder resin, 17 g of dipentaerythritol hexaacrylate as a polymerizable compound having ethylenically unsaturated bonds, 0.5 g of the photoactive compound 1 prepared in Example 1, whose is structure is shown in Table 3, and 70.5 g of PGMEA as an organic solvent were mixed together using a shaker for 3 hr.

TABLE 3

Compound 1

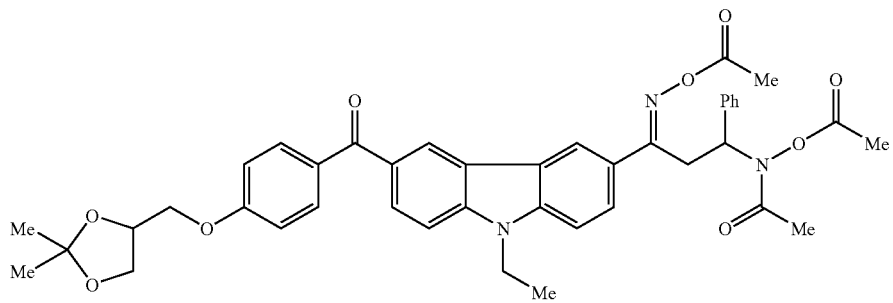

The mixture was filtered through a filter (size=5 microns) to obtain a photosensitive resin composition in the form of a solution. The photosensitive resin composition was applied to glass by spin coating, followed by prebaking at about 100° C. for 2 min to form a uniform film having a thickness of about 2.5 μm.

The film was exposed under a high-pressure mercury lamp with varying exposure doses from 40 to 100 mJ/cm$^2$ through a photomask having a circular isolated pattern. The exposed film was developed with an alkaline aqueous KOH solution (pH 11.3-11.7), washed with deionized water, and post-baked at 200° C. for about 40 min to form a pattern. The state of the pattern was observed with an optical microscope and a pattern profiler.

Comparative Example 4

A photosensitive resin composition was prepared in the same manner as in Example 2, except that 1 g of Irgacure 369 was used as a photopolymerization initiator instead of the compound 1.

Comparative Example 5

A photosensitive resin composition was prepared in the same manner as in Example 2, except that 1 g of Irgacure OXE-02 was used as a photopolymerization initiator instead of the compound 1.

Comparative Example 6

A photosensitive resin composition was prepared in the same manner as in Example 2, except that 1 g of the compound represented by the following formula was used as a photopolymerization initiator instead of the compound 1.

Evaluation of Physical Properties of the Photosensitive Resin Compositions

The physical properties of the transparent photosensitive resin compositions prepared in Example 2 and Comparative Examples 4-6 were measured in accordance with the following procedures, and the obtained results are shown in Table 4.

1. Photosensitivity

The sensitivity of each of the photosensitive resin compositions was defined as an exposure dose at which the pattern thickness was not increased any further when exposed to light with varying exposure doses through a photomask having a circular isolated pattern (diameter=30 μm). The lower the exposure dose, the better the sensitivity. The entire wavelength region of light from a high-pressure mercury lamp as a light source was used without filtering out any particular wavelength and the exposure dose was measured at 365 nm (i-line).

2. Residual Film Ratio

The residual film ratio was determined by measuring the thicknesses of the film before and after post baking.

Residual film ratio(%)=[(film thickness after post baking)/(film thickness before post baking)]×100

The higher the residual film ratio, the less the amount of contamination sources generated by decomposed products of the photopolymerization initiator in the subsequent processing step.

3. Mechanical Strength

After the pattern was indented with increasing force to 80 mN using a flat tip of a microhardness tester (H-100□, Fischerscope), the mechanical strength is defined as a variation in the thickness of the pattern.

Mechanical strength(%)=[(variation in thickness)/(film thickness before indentation)]×100

The smaller the thickness variation, the better the mechanical strength.

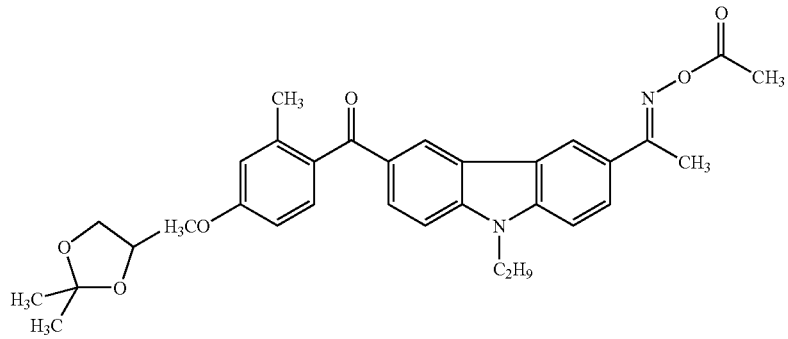

4. Heat Resistance

The heat resistance was determined by measuring the thicknesses of the film before and after storage in an oven at 200° C. for 40 min.

Heat resistance(%)=[(variation in thickness)/(film thickness before storage)]×100

The smaller the value, the better the heat resistance.

5. Chemical Resistance

The chemical resistance was determined by measuring the thicknesses of the pattern before and after dipping in N-methylpyrrolidone (NMP) at 70° C. for 1 min.

Chemical resistance(%)=[(variation in thickness)/(film thickness before dipping)]×100

The smaller the thickness variation, the better the chemical resistance.

6. Development Resistance

The development resistance was defined as a minimum size of the isolated pattern remaining after the film was exposed to a dose of 150 mJ/cm² and developed for 80 sec. The smaller the minimum size, the better the development resistance.

TABLE 4

| | Photosensitivity (mJ/cm²) | Residual film ratio (%) | Mechanical Strength (%) | Heat Resistance (%) | Chemical resistance (%) | Development resistance (μm) |
|---|---|---|---|---|---|---|
| Example 2 | 55 | 95 | 8 | 1.0 | 1.8 | 7 |
| Comparative Example 4 | 210 | 89 | 14 | 2.1 | 2.8 | 14 |
| Comparative Example 5 | 60 | 94 | 8 | 1.2 | 1.7 | 7 |
| Comparative Example 6 | 60 | 94 | 9 | 1.2 | 1.9 | 8 |

As can be seen from the results in Table 4, the transparent photosensitive composition of Example 2 showed better characteristics in terms of sensitivity, residual film ratio, mechanical strength, heat resistance, chemical resistance and development resistance than the photosensitive composition of Comparative Example 4. In addition, the sensitivity of the transparent photosensitive composition of Example 1 was better than that of the photosensitive composition of Comparative Example 5, which uses Irgacure OXE-02 known as the best one of the photoinitiator developed hitherto, and the residual film ratio, mechanical strength, heat resistance, chemical resistance and development resistance of the photosensitive composition of Example 2 were comparable or superior to those of the photosensitive composition of Comparative Example 5.

Particularly, the photosensitivity of the composition of Example 2 was 5 mJ/cm² better than that of the composition of Comparative Example 5. This indicates that the use of the composition of Example 2 shortens the time required for exposure and reduces the amount of the photoactive compound required for the same sensitivity as the composition of Comparative Example 5, leading to a reduction in preparation cost.

As is apparent from the foregoing, the photosensitive composition of the present invention has excellent characteristics in terms of sensitivity, residual film ratio, mechanical strength, heat resistance, chemical resistance and development resistance by the use of the photopolymerization initiator containing oxime ester moieties in one molecule. Therefore, the photosensitive composition of the present invention is advantageously used in curing materials for column spacers, overcoats and passivation films of liquid crystal display devices. In addition, the photosensitive composition of the present invention has excellent thermal processing characteristics.

What is claimed is:

1. A photoactive compound represented by Formula 1:

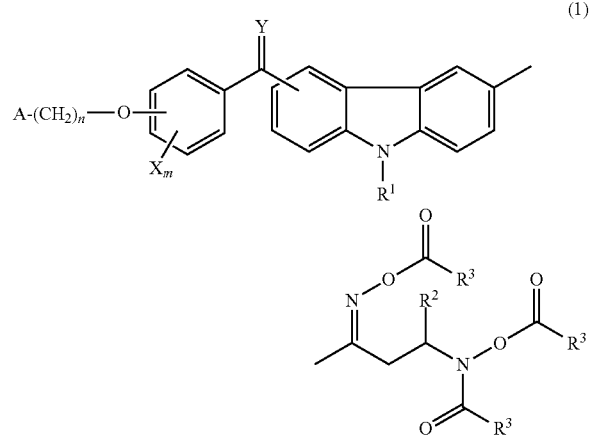

wherein $R^1$, $R^2$ and $R^3$ are each independently selected from the group consisting of a hydrogen atom, a halogen atom, OH, CN, R, OR, SR, COR, OCOR, NRR', CONRR', a substituted or unsubstituted phenyl group, and a $C_2$-$C_5$ alkylcarboxylic acid group, wherein R and R' are each independently $C_1$-$C_6$ alkyl; $C_1$-$C_6$ haloalkyl; or $C_1$-$C_6$ alkyl group substituted with at least one group selected from the group consisting of $NL_2$, OL and SL; wherein each L is hydrogen or $C_1$ to $C_6$ alkyl; and wherein the substituted phenyl is substituted with at least one group selected from the group consisting of $C_1$-$C_6$ alkyl, halogen atom, nitrile, OH and COOH, X is selected from the group consisting of a hydrogen atom; a halogen atom; a $C_1$-$C_6$ alkyl group unsubstituted or substituted with at least one group selected from the group wherein each L is hydrogen or $C_1$ to $C_6$ alkyl, consisting of $NL_2$, OL and SL; a $C_1$-$C_6$ haloalkyl group; a phenyl group unsubstituted or substituted with at least one group selected from the group consisting of $C_1$-$C_6$ alkyl, halogen atom, nitrile, OH and COOH; and a $C_2$-$C_5$ alkylcarboxylic acid group, Y is an oxygen atom or N—O—CO—$R^3$, A is selected from the group consisting of a cycloalkyl group, an aryl group, and a heterocyclic ring unsubstituted or substituted with at least one halogen atom or alkyl group, n is from 0 to 6, and m is from 0 to 4.

2. The photoactive compound of claim 1, wherein the heterocyclic ring is selected from the group consisting of 1,3-dioxolanyl, 2-tetrahydrofuryl, 3-tetrahydrofuryl, 2-tetrahy drothienyl, 2-oxalyl, 2-furyl, 3-furyl, 2-thienyl, 2-pyridyl, 2-piranyl, 2-carbazolyl, 2-pyrimidyl, and combinations thereof.

3. The photoactive compound of claim 1, wherein in Formula 1, $R^1$ is methyl or ethyl.

4. The photoactive compound of claim 1, wherein in Formula 1, $R^2$ is methyl or phenyl.

5. The photoactive compound of claim 1, wherein in Formula 1, $R^3$ is methyl or phenyl.

6. The photoactive compound of claim 1, wherein in Formula 1, X is hydrogen or methyl.

7. The photoactive compound of claim 1, wherein in Formula 1, Y is oxygen.

8. The photoactive compound of claim 1, wherein in Formula 1, A is selected from the group consisting of cyclohexyl, 2,2-dimethyl-1,3-dioxolanyl and 2-tetrahydrofuryl groups.

9. A photosensitive resin composition, comprising:
a photoactive compound represented by Formula 1:

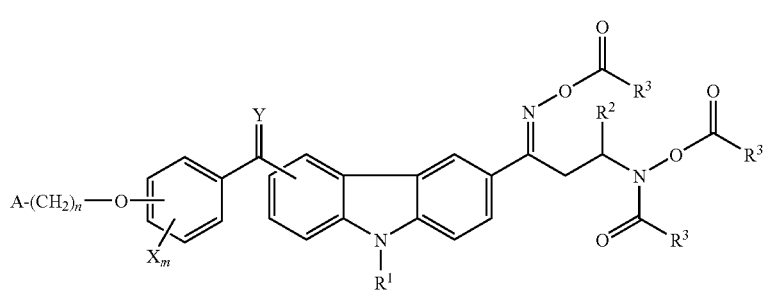

(1)

wherein $R^1$, $R^2$ and $R^3$ are each independently selected from the group consisting of a hydrogen atom, a halogen atom, OH, CN, R, OR, SR, COR, OCOR, NRR', CONRR', a substituted or unsubstituted phenyl group, and a $C_2$-$C_5$ alkylcarboxylic acid group, wherein R and R' are each independently $C_1$-$C_6$ alkyl; $C_1$-$C_6$ haloalkyl; or $C_1$-$C_6$ alkyl group substituted with at least one group selected from the group consisting of $NL_2$, OL and SL; wherein each L is hydrogen or $C_1$ to $C_6$ alkyl; and wherein the substituted phenyl is substituted with at least one group selected from the group consisting of $C_1$-$C_6$ alkyl, halogen atom, nitrile, OH and COOH, X is selected from the group consisting of a hydrogen atom; a halogen atom; a $C_1$-$C_6$ alkyl group unsubstituted or substituted with at least one group selected from the group consisting of $NL_2$, OL and SL; a $C_1$-$C_6$ haloalkyl group; a phenyl group unsubstituted or substituted with at least one group selected from the group wherein each L is hydrogen or $C_1$ to $C_6$ alkyl, consisting of $C_1$-$C_6$ alkyl, halogen atom, nitrile, OH and COOH; and a $C_2$-$C_5$ alkylcarboxylic acid group, Y is an oxygen atom or N—O—CO—$R^3$, A is selected from the group consisting of a cycloalkyl group, an aryl group, and a heterocyclic ring unsubstituted or substituted with at least one halogen atom or alkyl group, n is from 0 to 6, and m is from 0 to 4;

an alkali-soluble binder resin;

a polymerizable compound having at least one ethylenically unsaturated bond; and a solvent.

10. The photosensitive resin composition of claim 9, wherein the alkali-soluble binder resin has an acid value of 30 to 300 KOH mg/g and a weight average molecular weight of 1,000 to 200,000.

11. The photosensitive resin composition of claim 9, wherein the polymerizable compound having at least one ethylenically unsaturated bond is selected from the group consisting of: compounds obtained by esterifying an α,β-unsaturated carboxylic acid with a polyhydric alcohol selected from ethylene glycol di(meth)acrylate, polyethylene glycol di(meth)acrylate having 2 to 14 ethylene groups, trimethylolpropane di(meth)acrylate, trimethylolpropane tri(meth)acrylate, pentaerythritol tri(meth)acrylate, pentaerythritol tetra(meth)acrylate, 2-trisacryloyloxymethylethylphthalic acid, propylene glycol di(meth)acrylate having 2 to 14 propylene groups, dipentaerythritol penta(meth)acrylate, dipentaerythritol hexa(meth)acrylate, and a mixture of an acid modified product of dipentaerythritol penta(meth)acrylate and an acid modified product of dipentaerythritol hexa(meth)acrylate; compounds obtained by adding (meth)acrylic acid to a glycidyl group-containing compound; esterified products of a compound having at least one hydroxyl group or ethylenically unsaturated bond with a polyvalent carboxylic acid, and adducts thereof with polyisocyanate; alkyl esters of (meth)acrylic acid; 9,9'-bis[4-(2-acryloyloxyethoxy)phenyl]fluorene; and mixtures thereof.

12. The photosensitive resin composition of claim 9, wherein the photosensitive resin composition comprises 0.1 to 5% by weight of the photoactive compound of Formula 1, 1 to 20% by weight of the alkali-soluble binder resin, 0.5 to 20% by weight of the polymerizable compound having at least one ethylenically unsaturated bond, and 10 to 95% by weight of the solvent.

13. The photosensitive resin composition of claim 9, further comprising one or more additives selected from the group consisting of another photoactive compound, a curing accelerator, a thermal polymerization inhibitor, a plasticizer, an adhesion promoter, a filler, and a surfactant.

14. The photosensitive resin composition of claim 13, wherein the additional photoactive compound is selected from the group consisting of biimidazole compounds, acetophenone compounds, O-acyloxime compounds, benzophenone compounds, thioxanthone compounds, phosphine oxide compounds, coumarin compounds, and mixtures thereof.

15. The photosensitive resin composition of claim 13, wherein the additional photoactive compound is present in an amount of 0.1 to 5% by weight, based on the total weight of the photosensitive resin composition.

16. The photosensitive resin composition of claim 13, wherein the one or more additives selected from the curing accelerator, the thermal polymerization inhibitor, the plasticizer, the adhesion promoter, the filler and the surfactant are present in an amount of 0.01 to 5% by weight, based on the total weight of the photosensitive resin composition.

* * * * *